United States Patent
Kim (10) Patent No.: US 9,706,901 B2
(45) Date of Patent: Jul. 18, 2017

(54) INTERNAL DEVICE, EXTERNAL DEVICE, DIAGNOSIS APPARATUS INCLUDING THE SAME, AND ENDOSCOPE APPARATUS

(71) Applicant: Industry-Academic Cooperation Foundation, Yonsei University, Seoul (KR)

(72) Inventor: Tae Wook Kim, Seoul (KR)

(73) Assignee: Industry-Academic Cooperation Foundation, Younsei University, Seoul (KR)

( * ) Notice: Subject to any disclaimer, the term of this patent is extended or adjusted under 35 U.S.C. 154(b) by 282 days.

(21) Appl. No.: 14/609,303

(22) Filed: Jan. 29, 2015

(65) Prior Publication Data

US 2015/0208906 A1  Jul. 30, 2015

(30) Foreign Application Priority Data

Jan. 29, 2014  (KR) ........................ 10-2014-0011011

(51) Int. Cl.
  *A61B 1/04*  (2006.01)
  *A61B 1/00*  (2006.01)
  (Continued)

(52) U.S. Cl.
  CPC ...... *A61B 1/00006* (2013.01); *A61B 1/00036* (2013.01); *A61B 1/041* (2013.01); *A61B 5/061* (2013.01); *H04N 2005/2255* (2013.01)

(58) Field of Classification Search
  CPC combination set(s) only.
  See application file for complete search history.

(56) References Cited

U.S. PATENT DOCUMENTS 7,319,781 B2 * 1/2008 Chen ................. A61B 1/00009
  348/E7.09
2003/0085994 A1 * 5/2003 Fujita ................ A61B 1/00016
  348/77

(Continued)

FOREIGN PATENT DOCUMENTS

JP  2011-200283 A  10/2011
JP  4789762 B  10/2011

(Continued)

OTHER PUBLICATIONS

S. J. Lee, "Research on Localization of capsule endoscope using UWB transceivers", Ewha Woman's University, 2010.

*Primary Examiner* — Sath V Perungavoor
*Assistant Examiner* — Janese Duley
(74) *Attorney, Agent, or Firm* — Procopio, Cory, Hargreaves & Savitch LLP (57) ABSTRACT

Provided is a diagnosis apparatus. The diagnosis apparatus includes: an internal device inserted into an inside of a body and moving therein; and an external device located at an outside of the body and controlling the internal device, wherein the internal device includes: a first communication unit communicating with the external device; a power supply unit supplying power for driving of the internal device; and a first control unit controlling an operation of the internal device according to a control signal when the control signal is received from the external device, and the external device includes: a second communication unit communicating with the internal device; a location detection unit processing a signal received from the internal device to detect a location of the internal device; and a second control unit generating a control signal for controlling the internal device based on the location of the internal device.

16 Claims, 10 Drawing Sheets

(51) Int. Cl.
*A61B 5/06* (2006.01)
*H04N 5/225* (2006.01)

(56) References Cited

U.S. PATENT DOCUMENTS

| | | | | |
|---|---|---|---|---|
| 2007/0042716 | A1* | 2/2007 | Goodall | H04W 16/18 455/67.11 |
| 2007/0066868 | A1* | 3/2007 | Shikii | A61B 1/00036 600/118 |
| 2007/0255087 | A1* | 11/2007 | Minai | A61B 1/041 600/12 |
| 2009/0073260 | A1* | 3/2009 | Nagase | A61B 1/00009 348/68 |
| 2009/0299140 | A1* | 12/2009 | Wang | A61B 1/00009 600/118 |

FOREIGN PATENT DOCUMENTS

| | | |
|---|---|---|
| KR | 10-0884712 B | 5/2008 |
| KR | 10-1048916 B | 7/2011 |

* cited by examiner

INTERNAL DEVICE, EXTERNAL DEVICE, DIAGNOSIS APPARATUS INCLUDING THE SAME, AND ENDOSCOPE APPARATUS

CROSS-REFERENCE TO RELATED APPLICATIONS

This U.S. non-provisional patent application claims priority under 35 U.S.C. §119 of Korean Patent Application No. 10-2014-0011011, filed on Jan. 29, 2014, the entire contents of which are hereby incorporated by reference.

BACKGROUND OF THE INVENTION

The present invention disclosed herein relates to an internal device, an external device, a diagnosis apparatus comprising the same, and an endoscope apparatus.

Endoscopes that may immediately observe the inside of an organ or body cavity without an operation or autopsy are divided into general endoscopes that insert tubes having cameras at their ends into insides of bodies, and capsule endoscopes that patients swallow like tablets so that the endoscopes are inserted into the insides of the bodies. While general endoscopes causes pain and displeasure to patients when examination is performed, the capsule endoscopes supplement such a disadvantage of the general endoscopes and have an advantage in that it is possible to use for diagnosing, in particular, the small intestine.

However, it is difficult for the capsule endoscopes to recognize an accurate location inside a body and the capsule endoscopes continuously capture images of the inside of the body in order to track the location. However, due to the limited power of the capsule endoscopes, there is a need to decrease the resolution of a camera to generate an image having a low resolution in order to continuously capture images for a long time for which the capsule endoscopes stay at the inside of the body.

As a result, there was typically a limitation in discovering a lesion or diagnosing disease with the capsule endoscopes, and even if the lesion was discovered, there was a limitation in that it was difficult to recognize an accurate location.

SUMMARY OF THE INVENTION

The present invention provides an internal device, external device, diagnosis apparatus including the same, and endoscope apparatus that accurately detect the location of an internal device that is inserted into an inside of a body and moves therein, such as a capsule endoscope.

The present invention provides an internal device, external device, diagnosis apparatus including the same, and endoscope apparatus that control an internal device based on the location of the internal device to enhance control performance.

The present invention provides an internal device, external device, diagnosis apparatus including the same, and endoscope apparatus that provide information on an internal device to a user such as a patient or medical team based on the location of the internal device to enhance user convenience.

Embodiments of the present invention provide internal devices include a communication unit communicating with an external device located at an outside of a body; a power supply unit supplying power for the operating of the internal device; and a control unit controlling the operation of the internal device according to a control signal when the control signal is received from the external device.

In some embodiments, the communication unit may transmit or receive a signal wirelessly by using an antenna or through a body electrode by using an electrode.

In other embodiments, the internal devices may further include a camera unit capturing an image of an inside of the body.

In still other embodiments, the communication unit may transmit, to the external device, image data obtained through a corresponding image capturing operation whenever the camera unit captures an image.

In even other embodiments, the camera unit may start capturing an image in response to an image-capturing initiation request from the external device and finish capturing an image in response to an image-capturing stop request from the external device.

In yet other embodiments, the communication unit may transmit, to the external device, image data obtained from an image-capturing initiation request time to an image-capturing stop request time in response to the image-capturing stop request.

In further embodiments, the control unit may switch the internal device to an idle mode to decrease power consumption when a power-supply cutoff signal is received from the external device.

In still further embodiments, the control unit may switch the internal device to an operation mode to increase power consumption when a power-supply connection signal is received from the external device.

In even further embodiments, the control unit may cut off power supply from the power supply unit to the camera unit when a power supply cutoff signal is received from the external device, and enable the power supply unit to supply power to the camera unit when a power-supply connection signal is received from the external device.

In other embodiments of the present invention, external devices are located at an outside of a body and control an internal device and include a communication unit communicating with the internal device; a location detection unit processing a signal received from the internal device to detect a location of the internal device; and a control unit generating a control signal for controlling the internal device based on the location of the internal device.

In some embodiments, the communication unit may include at least three receivers located at different points on the body and receiving a signal from the internal device.

In other embodiments, the location detection unit may be configured to calculate a time difference of arrival of signals received from the internal device by each receiver, and detect the location of the internal device based on the time difference of arrival of received signals.

In still other embodiments, the receivers may be located on the same plane, and the communication unit may further include at least one secondary receiver located at another point on the body spaced apart from the same plane.

In even other embodiments, the receivers may be located at any one of front and rear sides of a human body, and the secondary receiver may be located at another one of the front and rear sides.

In yet other embodiments, the receivers may be located at any one of front and rear sides of a human body, and the secondary receiver may be located on a lateral face of the human body.

In further embodiments, the control unit may map the location of the internal device to a fluoroscopic image obtained by capturing an image of an inside of a body by using fluoroscopy to transmit, to a output device, the fluoroscopic image to which the location of the internal device is mapped.

In still further embodiments, the external device may further include a storage unit storing location information on at least one region inside a body, and the control unit may read the location information on the region from the storage unit, compare the location information with the location of the internal device, and determine a region in which the internal device is located.

In even further embodiments, the location information on the region may include location information on an organ inside a body.

In yet further embodiments, the control unit may transmit, to an output device, information on a region in which the internal device is located, to provide the information to a user.

In much further embodiments, the control unit may generate the control signal and transmit the control signal to the internal device when the region in which the internal device is located corresponds to a preset target region.

In still much further embodiments, the control unit may generate an alarm signal and transmit the alarm signal to an alarm device in order to provide an alarm to a user, when the region in which the internal device is located corresponds to a preset target region.

In even much further embodiments, the control unit may generate the alarm signal and transmit the alarm signal to the alarm device in order to enable a user to recognize that the internal device is discharged, when the region in which the internal device is located corresponds to a region from which the internal device is discharged to an outside of the body.

In yet much further embodiments, the control unit may generate an alarm signal and transmit the alarm signal to an alarm device in order to provide an alarm to a user, when a time for which the internal device stays at a preset region exceeds a preset limit In even other embodiments of the present invention, diagnosis apparatuses include an internal device inserted into an inside of a body and moving therein; and an external device located at an outside of the body and controlling the internal device, wherein the internal device includes: a first communication unit communicating with the external device; a power supply unit supplying power for driving of the internal device; and a first control unit controlling an operation of the internal device according to a control signal when the control signal is received from the external device, and the external device includes: a second communication unit communicating with the internal device; a location detection unit processing a signal received from the internal device to detect a location of the internal device; and a second control unit generating a control signal for controlling the internal device based on the location of the internal device.

In some embodiments, the second communication unit may include at least three receivers located at different points on the body and receiving a signal from the internal device.

In other embodiments, the location detection unit may be configured to calculate a time difference of arrival of signals received from the internal device by each receiver, and detect the location of the internal device based on the time difference of arrival of received signals.

In still other embodiments, the receivers may be located on the same plane, and the communication unit may further include at least one secondary receiver located at another point on the body spaced apart from the same plane.

In even other embodiments, the second control unit may map the location of the internal device to a fluoroscopic image obtained by capturing an image of an inside of a body by using fluoroscopy to transmit, to a output device, the fluoroscopic image to which the location of the internal device is mapped.

In yet other embodiments, the external device may further include a storage unit storing location information on at least one region inside a body, and the second control unit may read the location information on the region from the storage unit, compare the location information with the location of the internal device, and determine a region in which the internal device is located.

In further embodiments, the location information on the region may include location information on an organ inside a body.

In still further embodiments, the second control unit may transmit, to an output device, information on a region in which the internal device is located, to provide the information to a user.

In even further embodiments, the second control unit may generate a power-supply cutoff signal to transmit the signal to the internal device when the region in which the internal device is located corresponds to a first preset target region, and the first control unit may switch the internal device to an idle mode to decrease power consumption when the power-supply cutoff signal is received from the external device.

In yet further embodiments, the second control unit may generate a power-supply connection signal to transmit the signal to the internal device when the region in which the internal device is located corresponds to a second preset target region, and the first control unit may switch the internal device to an operation mode to increase power consumption when the power-supply connection signal is received from the external device.

In much further embodiments, the internal device may further include a camera unit capturing an image of an inside of a body, and the second control unit may generate and transmit a resolution control signal to the internal device to enable the camera unit to capture the image of the inside of the body at a first resolution when the region in which the internal device is located corresponds to a first target region, and at a second resolution lower than the first resolution when the region in which the internal device is located corresponds to a second target region.

In still much further embodiments, the second control unit may generate an alarm signal and transmit the alarm signal to an alarm device in order to provide an alarm to a user, when the region in which the internal device is located corresponds to a preset target region.

In even much further embodiments, the second control unit may generate the alarm signal and transmit the alarm signal to the alarm device in order to enable a user to recognize that the internal device is discharged, when the region in which the internal device is located corresponds to a region from which the internal device is discharged to an outside of the body.

In yet much further embodiments, the second control unit may generate an alarm signal and transmit the alarm signal to an alarm device in order to provide an alarm to a user, when a time for which the internal device stays at a preset region exceeds a preset limit In even other embodiments of the present invention, endoscope apparatuses may include a capsule endoscope inserted into an inside of a body and moving therein; a controller located at an outside of the body and controlling the capsule endoscope, wherein the capsule endoscope includes: a first communication unit communicating with the controller; a power supply unit supplying power for driving of the capsule endoscope; a camera unit capturing an image of an inside of the body; and a first control unit controlling an operation of the capsule endoscope according to a control signal when the control signal is received from the controller, and the controller includes: a second communication unit communicating with the capsule endoscope; a location detection unit processing a signal received from the capsule endoscope to detect a location of the capsule endoscope; and a second control unit generating a control signal for controlling the capsule endoscope based on the location of the capsule endoscope.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Embodiments of the present invention are described below in detail with reference to the drawings attached to the present disclosure.

Figure 1:
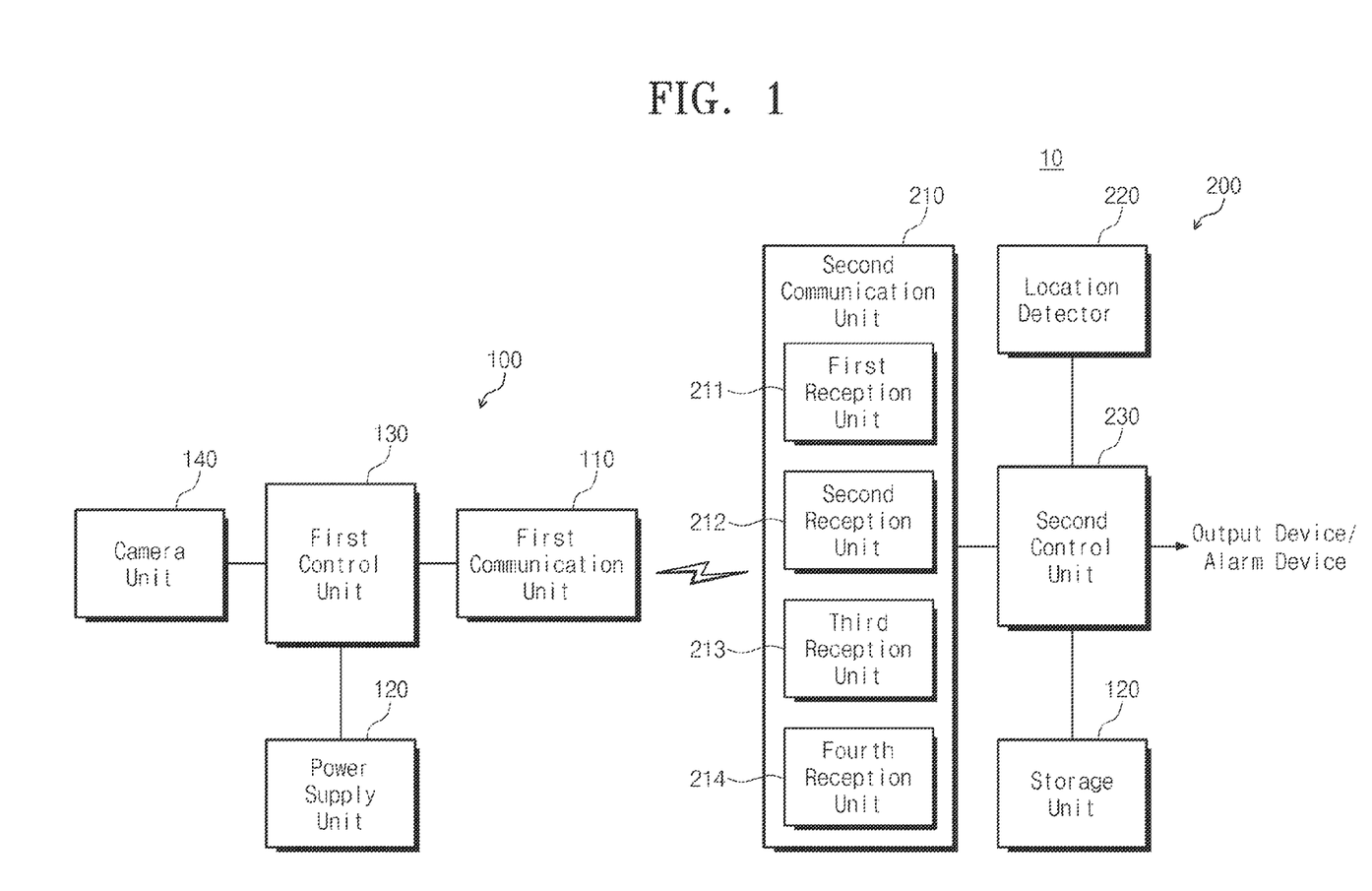
FIG. 1 is an exemplary block diagram of a diagnosis apparatus according to an embodiment of the present invention.

FIG. 1 is an exemplary block diagram of a diagnosis apparatus 10 according to an embodiment of the present invention.

As shown in FIG. 1, the diagnosis apparatus 10 may include an internal device 100 and an external device 200. The internal device 100 is inserted into the internal body and moves therein. The external device 200 is located at an outside of the body and controls the internal device 100.

According to an embodiment, the internal device 100 may be a capsule endoscope that includes a camera to capture images of the internal body. However, the internal device 100 is not limited to the capsule endoscope and includes all apparatuses inserted into the body to be used for diagnosis and therapy, such as a capsule-type surgical instrument including a surgical instrument, or a drug injection instrument injecting drug into an internal body.

Referring to FIG. 1, the internal device 100 may include a first communication unit 110, a power supply unit 120, and a first control unit 130. In addition, the external device 200 may include a second communication unit 210, a location detector 220, and a second control unit 230.

The first communication unit 110 may communicate with the external device 200. The power supply unit 120 may supply power for the operating of the internal device 100. The first control unit 130 may control the operation of the internal device 100 according to a control signal, when the control signal is received from the external device 200.

The second communication unit 210 may communicate with the internal device 100. The location detector 220 may process a signal received from the internal device 100 to detect the location of the internal device 100. The second control unit 230 may generate a control signal for controlling the internal device 100 based on the location of the internal device 100.

According to an embodiment, the first communication unit 110 may use an antenna to wirelessly transmit and receive a signal. However, the communication technique of the first communication unit 110 is not limited thereto and the first communication unit 110 may also use a body communication technique in which a signal is transmitted and received by using a body.

Likewise, the second communication unit 210 may also use an antenna to wirelessly transmit and receive a signal or use an electrode to transmit and receive a signal through a body.

The communication between the first communication unit 110 and the second communication unit 210 may use on off keying (OOK) modulation communicating according to the presence/absence of a pulse or pulse position modulation (PPM) communicating according to the location of a pulse but the communication technique is not limited thereto.

According to an embodiment of the present invention, the second communication unit 210 may include at least three receivers 211 to 213 that are located at different points on the body to receive signals from the internal device 100.

Figure 2:
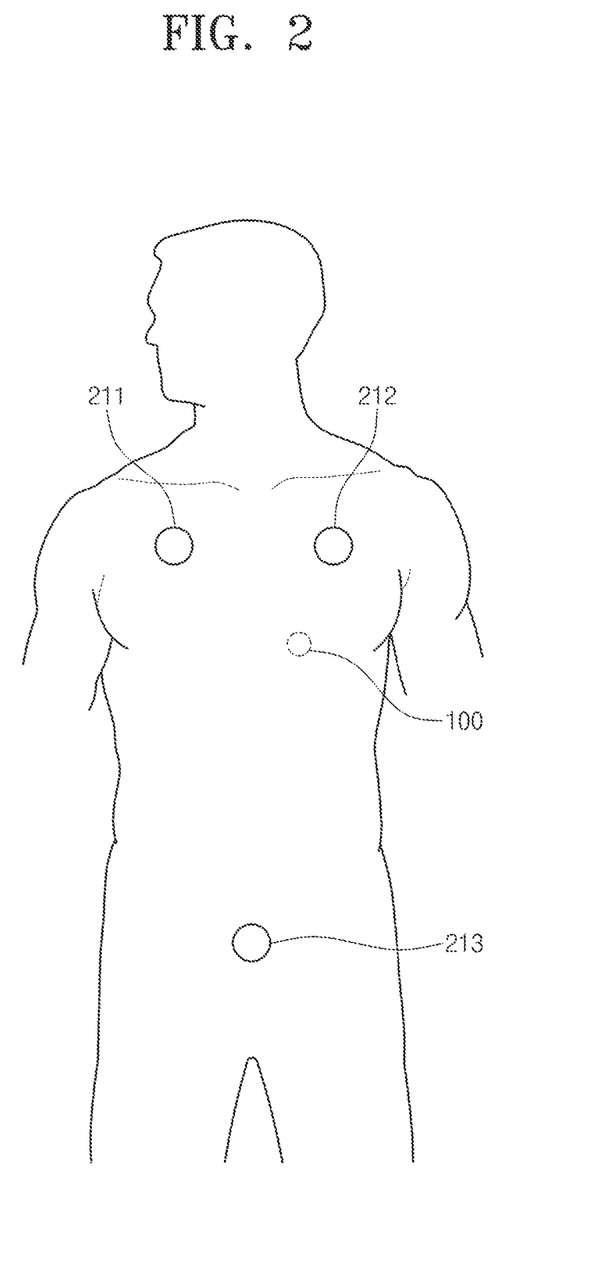
FIG. 2 is a diagram exemplarily representing where the receivers of an external device according to an embodiment of the present invention are located on the body.

FIG. 2 is a diagram exemplarily representing where the receivers 211 to 213 of the external device 200 according to an embodiment of the present invention are located on the body;

As shown in FIG. 2, the receivers 211 to 213 may be located at different points on the body of a patient into which the internal device 100 is inserted. The receivers 211 to 213 may be located at parts on which the relative location between receivers does not change even after the internal device 100 is inserted, one of the parts being the trunk of the patient, for example.

According to an embodiment of the present invention, the location detector 220 may calculate a time difference of arrival (TDOA) of signals received from the internal device 100 by each receiver, and detect the location of the internal device 100 based on the TODA of received signals. In other words, the location detector 220 may specify the location of the internal device 100 based on the TDOA of signals received from the at least three receivers 211 to 213.

Figure 3:
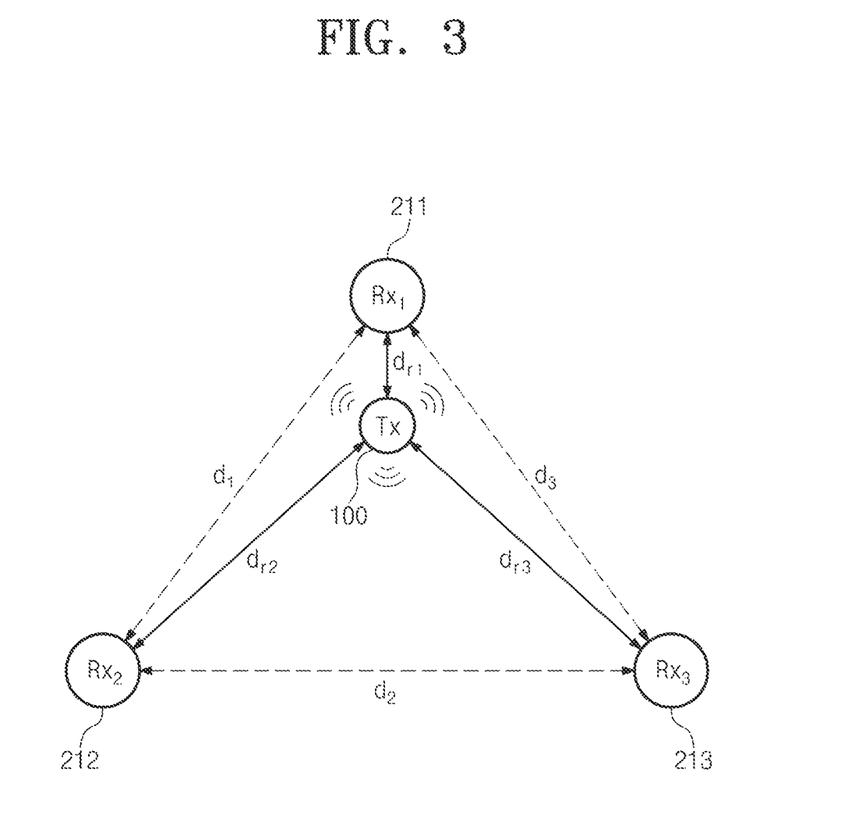
FIGS. 3 and 4 are exemplary diagrams for explaining the process of detecting the location of an internal device by an external device according to an embodiment of the present invention.
Figure 4:
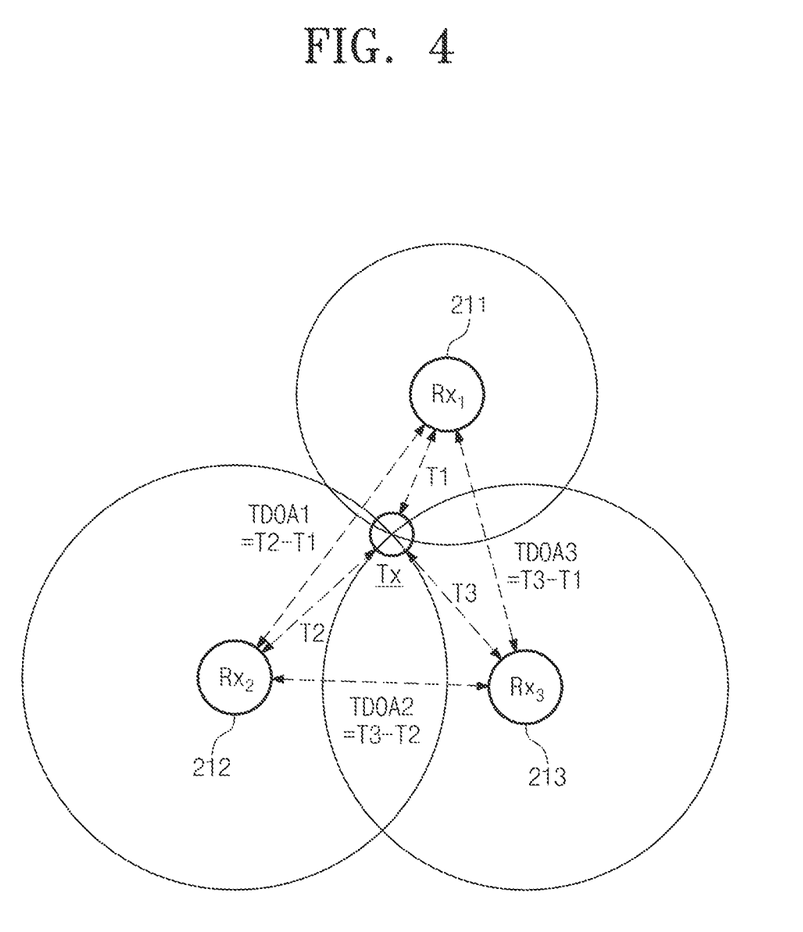

FIGS. 3 and 4 are exemplary diagrams for explaining the process of detecting the location of the internal device 100 by the external device 200 according to an embodiment of the present invention.

As shown in FIG. 3, the relative location relationship including the distance d1, d2 or d3 between the receivers 211 to 213 is previously known information. When the internal device 100 inserted into the internal body transmits a signal, the receivers 211 to 213 receive signals after arrival times $T_1$ to $T_3$ determined according to distances $d_{r1}$ to $d_{r3}$ from the internal device 100.

Then, as shown in FIG. 4, the location detector 220 may calculate $TDOA_1$ to $TDOA_3$ of signals received by each receiver and detect the location of the internal device 100 determined according to the $TDOA_1$ to $TDOA_3$.

The first communication unit 110 and the second communication unit 210 operate with mutually independent clocks, and the receivers 211 to 213 may share the same clock.

According to an embodiment of the present invention, the receivers 211 to 213 may be located on the same plane. For example, as shown in FIG. 2, the receivers 211 to 213 may be located on any one of the front and rear sides of the human body.

According to another embodiment of the present invention, the first communication unit 210 may further include at least one secondary receiver.

The secondary receiver may be located at another point on the body which is at a certain interval from the same plane on which the receivers 211 to 213 are located.

Figure 5:
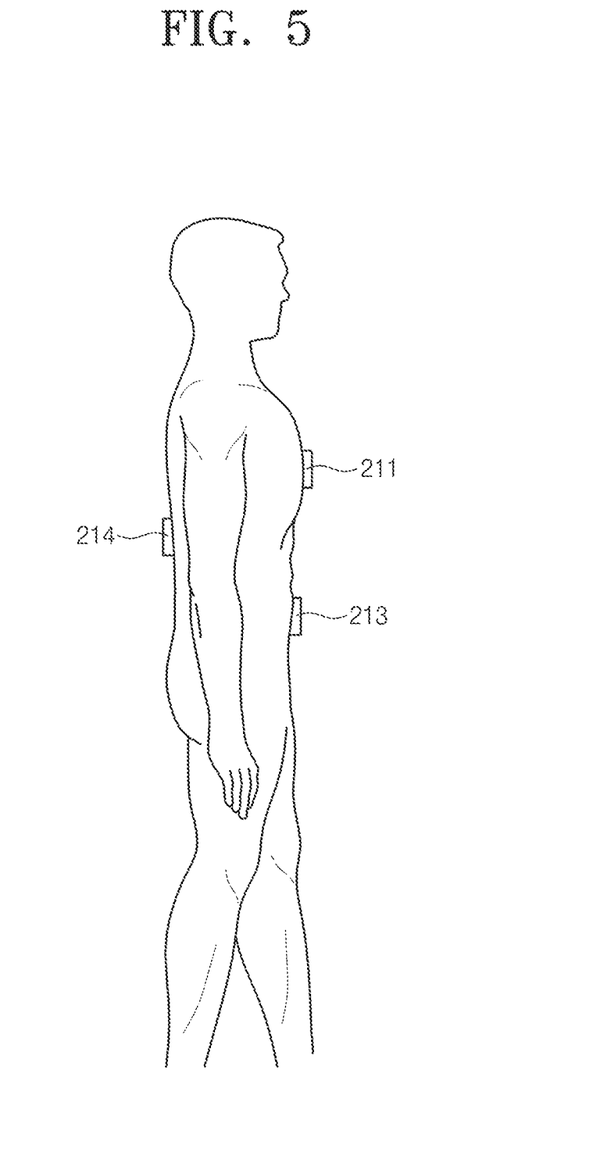
FIGS. 5 and 6 are diagrams exemplarily representing where the receivers of an external device according to another embodiment of the present invention and a secondary receiver are located on the body.
Figure 6:
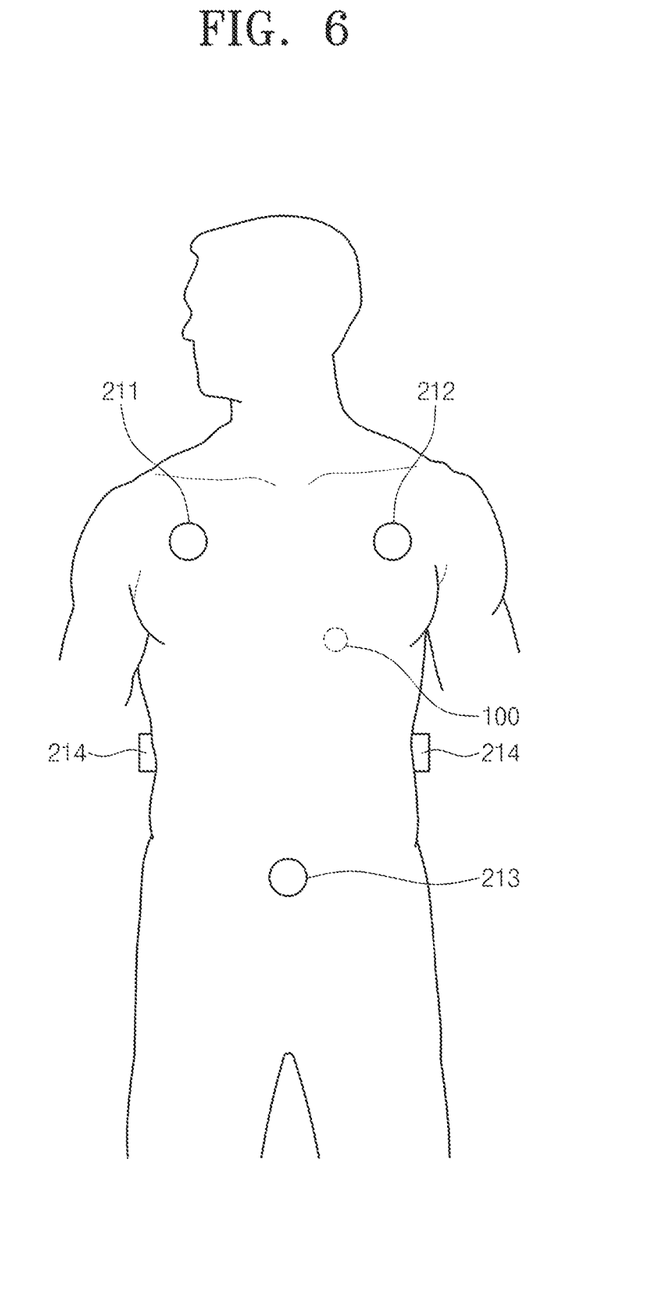

FIGS. 5 and 6 are diagrams exemplarily representing where the receivers 211 to 213 of the external device 200 according to another embodiment of the present invention and a secondary receiver 214 are located on the body.

According to an embodiment, the receivers 211 to 213 may be located at any one of the front and rear sides of the human body and the secondary receiver 214 may be located on the other of the front and rear sides. For example, as shown in FIG. 5, the receivers 211 to 213 may be located on the front side of the human body and the secondary receiver 214 may be located on the rear side.

According to another embodiment, the receivers 211 to 213 may be located at any one of the front and rear sides of the human body and the secondary receiver 214 may be located on a lateral side of the human body. For example, as shown in FIG. 6, the receivers 211 to 213 may be located on the front side of the human body and the secondary receiver 214 may be located on the waist.

As such, when at least one secondary receiver 214 in addition to the at least three receivers 211 to 213 is disposed on a plane different from the plane on which the receivers are located, the external device 200 may detect 3D coordinate information including a depth in addition to 2D coordinate information on the plane of the internal device 100.

The receivers 211 to 213 and the secondary receiver 214 may be attached to the body, but the present invention is not limited thereto and the receivers 211 to 213 and the secondary receiver 214 may also be put on the body and installed on the bed on which a patient lies.

According to an embodiment of the present invention, the second control unit 230 may map the location of the internal device 100 to a fluoroscopic image obtained by capturing images of the internal body using fluoroscopy to transmit, to an output device, the fluoroscopic image to which the location of the internal device 100 is mapped.

Figure 7:
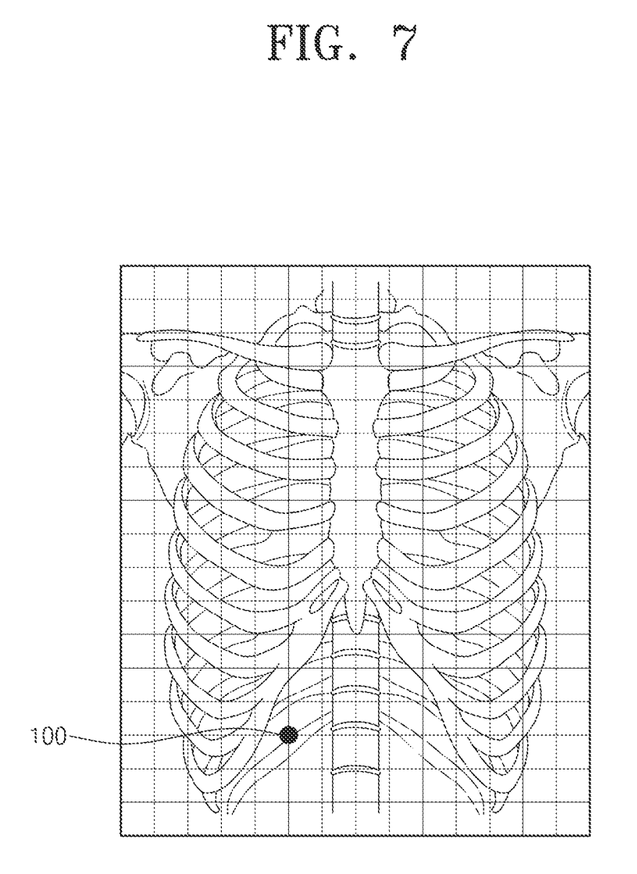
FIG. 7 is a diagram exemplarily representing a fluoroscopic image of an inside of a body to which the location of an internal device according to an embodiment of the present invention is mapped.

FIG. 7 is a diagram exemplarily representing a fluoroscopic image of the inside of the body to which the location of the internal device 100 according to an embodiment of the present invention is mapped.

As shown in FIG. 7, the internal device 100 may map the location of the internal device to a fluoroscopic image obtained by capturing images of the internal body using fluoroscopy, transmit the fluoroscopic image to an output device, for example, a display to display the fluoroscopic image.

According to an embodiment, the fluoroscopic image may be an X-ray image, but the present invention is not limited thereto and the fluoroscopic image includes any images representing the appearance of the inside of the body, for example, an ultrasonic image, a CT image or an MRI image.

The second control unit 230 may mark the internal device 100 on the fluoroscopic image based on coordinates corresponding to the location of the internal device 100 to map the internal device 100 to the fluoroscopic image.

To this end, the second control unit 230 may configure the coordinates system of the internal device 100 based on a point identifiable on the fluoroscopic image.

Figure 8:
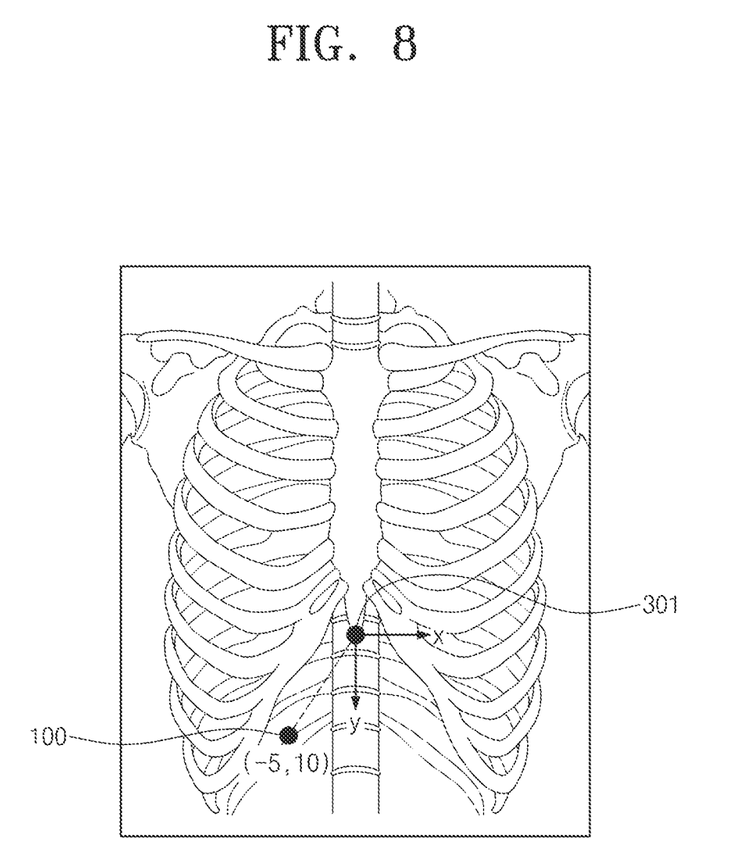
FIG. 8 is an exemplary diagram for explaining the process of calculating the coordinates of an internal device according to an embodiment of the present invention.

FIG. 8 is an exemplary diagram for explaining the process of calculating the coordinates of the internal device 100 according to an embodiment of the present invention.

As shown in FIG. 8, the second control unit 230 may use a part identifiable on the fluoroscopic image to configure a coordinates system.

For example, the second control unit 230 may configure a coordinates system having xiphoid process 301 as a starting point, and it is possible to calculate coordinates (−5, 5) corresponding to the location of the internal device 100 on the coordinates system.

Then, the second control unit 230 may identify the point set as the starting point of the coordinates system on the fluoroscopic image, configure a coordinates system having an identified point as a starting point, and then mark a marker on a point corresponding to the coordinates (−5, 10) of the internal device 100 on the coordinates system to map the location of the internal device 100 to the fluoroscopic image.

Referring back to FIG. 1, the external device 200 may further include a storage unit 240.

According to an embodiment, the storage unit 240 may store the fluoroscopic image of a patient into which the internal device 100 is inserted. In this case, the second control unit 230 may read the fluoroscopic image from the storage unit 240 to map the location of the internal device 100 to the fluoroscopic image, and then transmit a mapped fluoroscopic image to an output device.

According to another embodiment, the storage unit 240 may store location information on at least one region inside the body.

In this case, the second control unit 230 may read location information on the region from the storage unit 240 to compare the location information with the location of the internal device 100 and determine at which region the internal device 100 is located.

Figure 9:
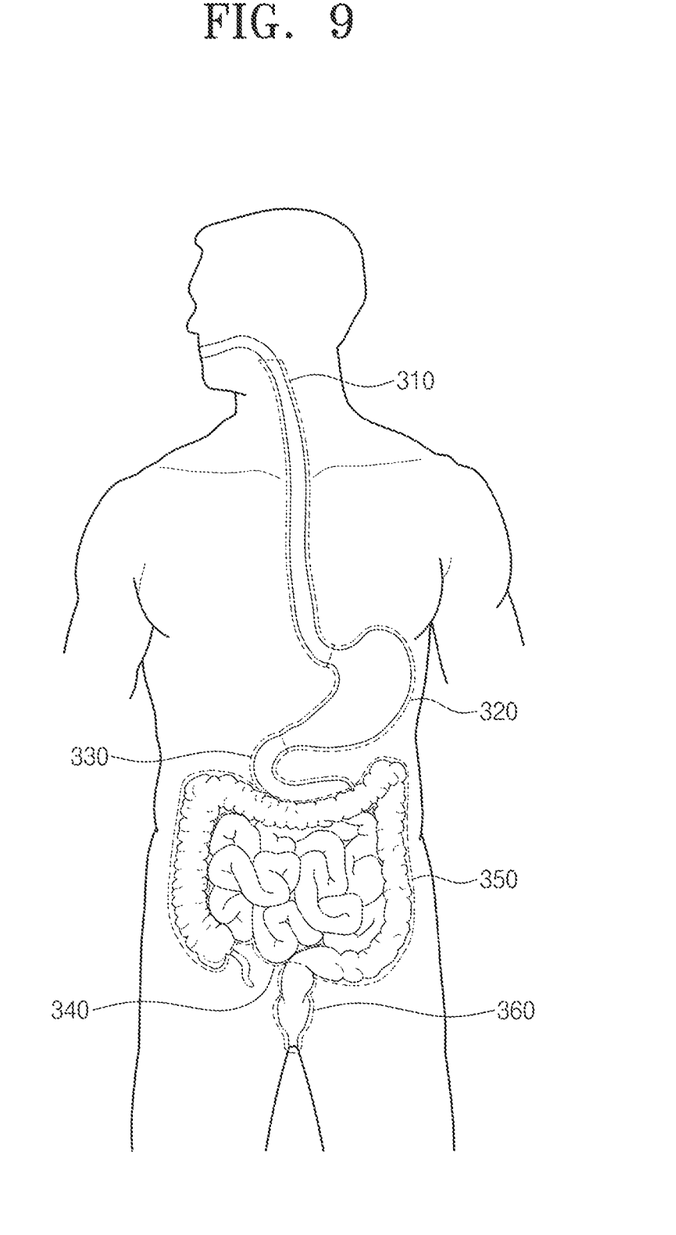
FIG. 9 is a diagram exemplarily representing internal regions partitioned according to an embodiment of the present invention.

FIG. 9 is a diagram exemplarily representing internal regions partitioned according to an embodiment of the present invention.

As shown in FIG. 9, the internal body of a patient into which the internal device 100 is inserted may be previously divided into one or more regions, and location information on each region may be stored in the storage unit 240.

According to an embodiment, the location information on the region may include location information on an organ inside the body. In FIG. 9, the regions are divided into an esophagus region 310, a stomach region 320, a duodenum region 330, a small intestine region 340, a large intestine region 350 and a rectum region 360 that form a digestive system, for example.

The second control unit 230 may read location information on the region from the storage unit 240 to compare the location information with the location of the internal device 100 and determine at which region the internal device 100 is located.

For example, the second control unit 230 may read the coordinates of the regions 310 to 360 from the storage unit 240, compare the coordinates with the coordinate of the internal device 100, and determine at which region the internal device 100 is located.

According to an embodiment, the second control unit 230 may transmit information on at which region the internal device 100 is located, to an output device to provide the information to a user. As a result, a medical team may manipulate the internal device 100 or recognize the location of a lesion, checking through the output device at which region the internal device 100 is located.

According to another embodiment of the present invention, the second control unit 230 may generate a power-supply cutoff signal to transmit the signal to the internal device 100 when the region at which the internal device 100 is located corresponds to a first preset target region.

The power-supply cutoff signal may be transmitted through the first and second communication units 110 and 210, and the first control unit 130 may switch the internal device 100 to an idle mode to decrease the amount of power consumption when the power-supply cutoff signal is received from the external device 200.

For example, when the internal device 100 is used to capture images of the small intestine only and the internal device 100 is located at the esophagus region 310, the stomach region 320, and the duodenum region 330, the second control unit 230 may generate a power-supply cutoff signal to transmit the signal to the internal device 100, and the first control unit 130 may switch the internal device 100 to an idle mode in response to the power-supply cutoff signal.

Then, the second control unit 230 may generate a power-supply connection signal to transmit the signal to the internal device 100 when the region at which the internal device 100 is located corresponds to a second preset target region.

The power-supply connection signal may also be transmitted through the first and second communication units 110 and 210, and the first control unit 130 may switch the internal device 100 to a working mode to increase the amount of power consumption when the power-supply connection signal is received from the external device 200.

For example, when the internal device 100 passes through the duodenum region 330 and then enters the small intestine region 340, the second control unit 230 may generate a power-supply connection signal to transmit the signal to the internal device 100 and the first control unit 130 may switch the internal device 100 to a working mode in response to the power-supply connection signal.

Then, when the internal device 100 passes through the small intestine region 340 and then enters the large intestine region 350, the second control unit 230 may re-generate a power-supply cutoff signal to transmit the signal to the internal device 100 and the first control unit 130 may switch the internal device 100 to an idle mode in response to the power-supply cutoff signal.

Although the power supply of the internal device 100 is controlled based on the location of the internal device 100 in the above-described embodiment, it is also possible to control other operations of the internal device 100 besides the power supply according to an embodiment.

As an example, when the internal device 100 is a capsule endoscope including the camera unit 140, the diagnosis apparatus 10 may control the operations of the camera unit 140 based on the location of the internal device 100. For example, when the internal device 100 is located at a target region, for example, the small intestine 340, the diagnosis apparatus 10 may enable the camera unit 140 to capture images of the internal body.

According to an embodiment, the diagnosis apparatus 10 may also control the resolution of images of the internal body captured by the camera unit 140 based on the location of the internal device 100.

For example, when the region at which the internal device 100 is located corresponds to a first preset target region (for example, the small intestine 340), the camera unit 140 may capture images of the internal body at a first resolution, and when the region at which the internal device 100 is located corresponds to a second preset target region (for example, other regions excluding the small intestine 340), the second control unit 230 may generate a resolution control signal to transmit the signal to the internal device 100 so that the camera unit 140 captures images of the internal body at a second resolution lower than the first resolution.

As a result, the diagnosis apparatus 10 may selectively increase the resolution of an image on only a region to be captured with the internal device 100 to reduce the amount of power consumption.

As another example, when the internal device 100 is a surgical apparatus including a surgical instrument, the diagnosis apparatus 10 may control the surgical instrument based on the location of the internal device 100. For example, a medical team may manipulate the surgical instrument, checking the location of the internal device 100.

As another example, when the internal device 100 is a drug injector injecting a drug, the diagnosis apparatus 10 may determine when to inject the drug, based on the location of the internal device 100. For example, when the internal device 100 is located at a target region, for example, a diseased part, the diagnosis apparatus 10 may enable the internal device 100 to discharge the drug so that the drug may be injected into a desired part.

According to another embodiment of the present invention, the second control unit 230 may generate an alarm signal to provide an alarm to a user and transmit the signal to an alarm device, when the region at which the internal device 100 is located corresponds to a preset target region.

Figure 10:
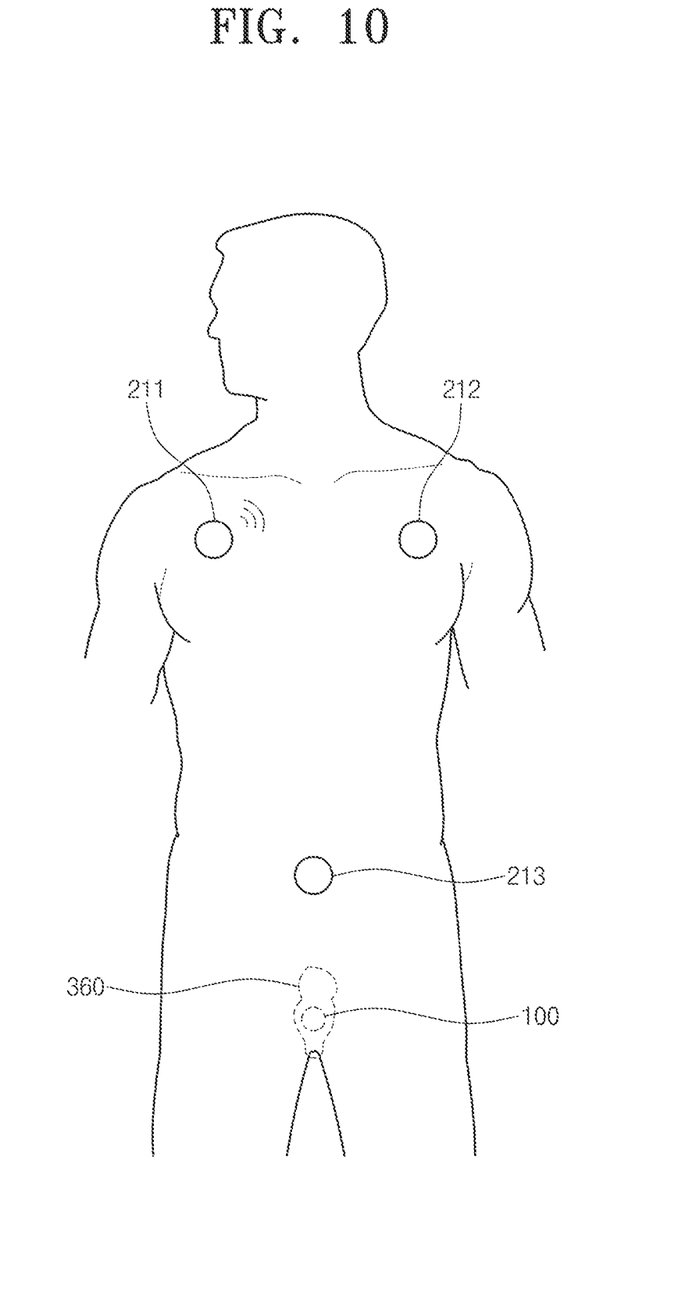
FIG. 10 is a diagram exemplarily representing how to enable a user to recognize that an internal device is discharged according to an embodiment of the present invention.

FIG. 10 is a diagram exemplarily representing how to enable a user to recognize that the internal device is discharged according to an embodiment of the present invention.

As shown in FIG. 10, the second control unit 230 may generate an alarm signal to provide to a user a notice that the internal device 100 is discharged to the outside of the body, and transmit the signal to an alarm device, when the region at which the internal device 100 is located corresponds to a region from which the internal device 100 is discharged to the outside of the body, for example, the rectum region 360.

According to an embodiment, the external device 200 may further include an alarm unit, for example, a speaker, generating and outputting an alarm, and the alarm unit may generate and output the alarm when an alarm signal is received from the second control unit 230.

As such, the diagnosis apparatus 10 may provide an alarm to a user according to the location of the internal device 100 so that the user may take necessary measures according to the location of the internal device 100. For example, when the user recognizes the alarm alerting that the internal device 100 is discharged, he or she may easily retrieve the internal device 100 by having a careful bowel movement.

According to another embodiment of the present invention, the second control unit 230 may generate an alarm signal to provide an alarm to a user and transmit the signal to an alarm device, when a time for which the internal device 100 stays at a preset region is beyond a preset limit For example, when the internal device 100 stays at a region inside the body for a long time and has no motion, there is a need to take a measure for promoting the movement of the internal device 100. As such, when the internal device 100 stays at a certain region beyond the limit, the second control unit 230 may sense it and thus provide an alarm to a user.

According to an embodiment, the diagnosis apparatus 10 may be an endoscope apparatus including a capsule endoscope and a controller controlling the capsule endoscope. In this case, the internal device 100 may correspond to the capsule endoscope and the external device 200 may correspond to the controller.

In addition, the capsule endoscope may further include the camera unit 140 capturing images of the internal body in addition to the first communication unit 110, the power supply unit 120, and the first control unit 130.

The first communication unit 110 may transmit, to the controller, image data obtained through each image capturing operation whenever the camera unit 140 captures an image. The controller may detect the location of the capsule endoscope based on a signal used for the transmission of the image data.

According to an embodiment, the camera unit 140 may start capturing an image in response to an image-capturing initiation request from the controller and finish capturing an image in response to an image-capturing stop request from the controller. In this case, the first communication unit 110 may transmit image data obtained from an image-capturing initiation request time to an image-capturing stop request time to the controller in response to the image-capturing stop request.

Also, when a power-supply cutoff signal is received from the controller, the first control unit 130 may cut off power supply from the power supply unit 120 to the camera unit 140 when the power-supply cutoff signal is received from the controller, and the first control unit may also enable the power supply unit 120 to supply power to the camera unit 140 when a power-supply connection signal is received from the controller.

According to an embodiment of the present invention, it is possible to accurately detect the location of the internal device that is inserted into the internal body and moves therein.

According to an embodiment of the present invention, it is possible to enhance the control performance of the internal device based on the location of the internal device and decrease the amount of power consumption.

According to an embodiment of the present invention, it is possible to provide information on the internal device to a user based on the location of the internal device to enhance user convenience.

Although the present invention is described above through embodiments, the embodiments above are only provided to describe the spirit of the present invention and not intended to limit the present invention. A person skilled in the art would understand that various modifications to the above-described embodiments may be implemented. The scope of the present invention is defined only by the following claims.

What is claimed is:

1. An internal device inserted into an inside of a body and to move therein, the internal device comprising a processor configured to:
   communicating with an external device located at an outside of the body;
   supplying power for driving of the internal device; and
   controlling an operation of the internal device according to a control signal when the control signal is received from the external device,
   wherein the processor receives, from the external device, a resolution control signal for enabling the internal device to selectively increase the resolution of an image on only a region to be captured with the internal device.

2. The internal device of claim 1, wherein the processor transmits and receives a signal wirelessly by using an antenna or through the body by using an electrode.

3. The internal device of claim 1, further comprising a camera configured to capture an image of the inside of the body.

4. The internal device of claim 3, wherein the processor transmits, to the external device, image data obtained through a corresponding image-capturing operation whenever the camera captures an image.

5. The internal device of claim 3, wherein the camera starts to capture an image in response to an image-capturing initiation request from the external device and finishes to capture an image in response to an image-capturing stop request from the external device.

6. The internal device of claim 5, wherein the processor transmits image data obtained from an image-capturing start request time to an image-capturing stop request time to the controller in response to the image-capturing stop request.

7. The internal device of claim 1, wherein the processor switches the internal device to an idle mode to reduce power consumption, when a power cutoff signal is received from the external device.

8. The internal device of claim 7, wherein the processor switches the internal device to an operation mode to increase power consumption, when a power-supply connection signal is received from the external device.

9. The internal device of claim 3, wherein the processor cuts off power supply to the camera when a power-supply cutoff signal is received from the external device, and supplies power to the camera when a power-supply connection signal is received from the external device.

10. An external device located at an outside of a body and to control an internal device inserted into an inside of the body and to move therein, the external device comprising a processor configured to:
    communicate with the internal device;
    processing a signal received from the internal device to detect a location of the internal device; and
    generating a control signal for controlling the internal device based on the location of the internal device,
    wherein the processor generates a resolution control signal for enabling the internal device to selectively increase the resolution of an image on only a region to be captured with the internal device.

11. The external device of claim 10, wherein the processor controls at least three receivers located at different points on the body and receives a signal from the internal device via the at least three receivers.

12. The internal device of claim 11, wherein the processor calculates a difference between times when the processor receives a signal from the internal device via each receiver, and detects the location of the internal device based on a time difference between received signals.

13. The external device of claim 11, wherein the receivers are located on the same plane, and
the processor controls at least one secondary receiver located at another point on the body spaced apart from the same plane.

14. The external device of claim 13, wherein the receivers are located at any one of front and rear sides of a human body, and
the secondary receiver is located at another one of the front and rear sides.

15. The external device of claim 13, wherein the receivers are located at any one of front and rear sides of a human body, and
the secondary receiver is located on a lateral face of the human body.

16. A diagnosis apparatus comprising:
an internal device inserted into an inside of a body and to move therein; and
an external device located at an outside of the body and to control the internal device,
wherein the internal device comprises a first processor configured to:
communicate with the external device;
supply power for driving of the internal device; and
control an operation of the internal device according to a control signal when the control signal is received from the external device, and
the external device comprises a second processor configured to:
communicate with the internal device;
process a signal received from the internal device to detect a location of the internal device; and
generate a control signal for controlling the internal device based on the location of the internal device,
wherein the second processor generates a resolution control signal for enabling the internal device to selectively increase the resolution of an image on only a region to be captured with the internal device.

* * * * *